United States Patent [19]
Gregg et al.

[11] Patent Number: 5,262,035
[45] Date of Patent: Nov. 16, 1993

[54] ENZYME ELECTRODES

[75] Inventors: Brian A. Gregg; Adam Heller, both of Austin, Tex.

[73] Assignee: E. Heller and Company, Austin, Tex.

[21] Appl. No.: 389,226

[22] Filed: Aug. 2, 1989

[51] Int. Cl.$^5$ .......................................... G01N 27/327
[52] U.S. Cl. ........................... 204/403; 204/153.12; 435/817; 436/518; 436/531; 436/806
[58] Field of Search ..................... 204/153.12, 403; 435/817; 436/806, 518, 531

[56] References Cited

U.S. PATENT DOCUMENTS

| | | | |
|---|---|---|---|
| 4,224,125 | 9/1980 | Nakamura et al. | 435/817 |
| 4,461,691 | 7/1984 | Frank | 204/290 R |
| 4,476,003 | 10/1984 | Frank et al. | 204/290 R |
| 4,524,114 | 6/1985 | Samuels et al. | 204/294 |
| 4,545,382 | 10/1985 | Higgins et al. | 204/403 |
| 4,619,754 | 10/1986 | Niki et al. | 204/290 R |
| 4,655,885 | 4/1987 | Hill et al. | 204/290 R |
| 4,711,245 | 12/1987 | Higgins et al. | 204/415 |
| 4,717,673 | 1/1988 | Wrighton et al. | 204/290 F |
| 4,721,601 | 1/1988 | Wrighton et al. | 204/435 |
| 4,764,416 | 8/1988 | Ueyama et al. | 428/212 |
| 4,784,736 | 11/1988 | Lonsdale et al. | 204/157.15 |
| 4,894,339 | 1/1990 | Hawazato et al. | 435/817 |
| 4,917,800 | 4/1990 | Lonsdale et al. | 210/490 |
| 4,968,400 | 11/1990 | Shimomura et al. | 204/403 |
| 5,089,112 | 2/1992 | Skotheim et al. | 204/153.12 |

FOREIGN PATENT DOCUMENTS

| | | |
|---|---|---|
| 127958A2 | 5/1984 | European Pat. Off. . |
| 0125139 | 11/1984 | European Pat. Off. . |
| 0184909 | 6/1986 | European Pat. Off. . |
| 0241309A3 | 4/1987 | European Pat. Off. . |
| 0278647 | 8/1988 | European Pat. Off. . |
| 0368209A1 | 6/1989 | European Pat. Off. . |
| 0390390A1 | 3/1990 | European Pat. Off. . |
| 55-012437A | 1/1980 | Japan . |
| 83049821B | 11/1983 | Japan . |
| 63-309848A | 12/1988 | Japan . |
| 2-006737A | 1/1990 | Japan . |
| 2-088960A | 3/1990 | Japan . |
| 2099850A | 4/1990 | Japan . |
| 830229A | 5/1981 | U.S.S.R. . |

OTHER PUBLICATIONS

Anson et al., *J. of the Am. Chem. Soc.*, vol. 105, No. 15, (1983), pp. 4883–4890.

Anson et al., *J. of the Am. Chem. Soc.*, vol. 105, No. 5, (1983), pp. 1096–1106.

Foulds, et al., Immobilization of Glucose Onidase in Ferrocene-Modified Pyrrole Polymers, Anal. Chem., vol. 60, No. 22, 2473–8 (1988).

Hale, et al., A New Class of Amperometric Biosensor Incorporating a Polymeric Electron-Transfer Mediator, J. Am. Chem. Soc., vol. 111, No. 9, pp. 3482–3484 (1989).

Foulds, et al., Enzyme Entrapment in Electrically Conducting Polymers, J. Chem. Soc., Faraday Trans. 1, vol. 82, pp. 1259–1264 (1986).

Degani, et al., Electrical Communication Between Redox Centers of Glucose Oxidase and Electrodes via Electrostatically and Covalently Bond Redox Polymers, J. Am. Chem. Soc., vol. 111, pp. 2357–2358 (1989).

Bartlett, et al., Strategies for the Development of Amperometric Enzyme Electrodes, Biosensors, vol. 3, pp. 359–379 (1987/88).

Clark, et al., Electrode Systems for Continuous Monitoring in Cardiovascular Surgery, Ann N.Y. Acad. Sci., vol. 102, pp. 29–45 (1962).

Clark, et al., Long-term Stability of Electroenzymatic Glucose Sensors Implanted in Mice Trans. Am. Soc. Artif. Inten. Organs, vol. 34, pp. 259–265 (1988).

(List continued on next page.)

Primary Examiner—T. Tung
Attorney, Agent, or Firm—Pravel, Hewitt, Kimball & Krieger

[57] ABSTRACT

Enzyme electrodes having a surface coated with a film. The film is formed from materials in which a redox enzyme is covalently bonded to a three dimensional molecular structure. The molecular structure is of the class having multiple redox centers, for example, a crosslinked redox polymer.

18 Claims, 6 Drawing Sheets

OTHER PUBLICATIONS

Cass, et al., Ferricinium as an Electron Acceptor for Oxido-Reductases, J. Electroanal. Chem., vol. 190, pp. 117–127 (1985).

Albery, et al., Amperometric Enzyme Electrodes, Phil. Trans. R. Soc. Lond., vol. B 316, pp. 107–119 (1987).

Scheller, et al., Enzyme Electrodes and Their Application, Phil. Trans. R. Soc. Lond, vol. B 316, pp. 85–94 (1987).

Pollak, et al., Enzyme Immobilization by Condensation Copolymerization into Cross-Linked Polyacrylamide Gels, J. Am. Chem. Soc., vol. 102, No. 20, pp. 6324–6336 (1980).

Castner, et al. Mass Transport and Reaction Kinetic Parameters Determined Electrochemically for Immobilized Glucose Oxidase, Biochemistry, vol. 23, No. 10, pp. 2203–2210 (1984).

Gregg et al., "Cross-Linked Redox Gels Containing Glucose Oxidase for Amperometric Biosensor Applications", 1990, pp. 258–263.

Coughlan, "Concepts and Approahces to the Understanding of Electron Transfer Processes in Enzymes Containing Multiple Redox Centers", 1980, Chapter 5, *Molybdenum-Containing Enzymes*, pp. 187–220.

Bartlett, et al., "Covalent Binding of Electron Relays to Glucose Oxidase," J. Chem. Soc., Chem. Commun., pp. 1693–2004 (1987).

Umana, U.S. Army Research Office Report No. ARO 23106.3-LS entitled "Protein-Modified Electrochemically Active Biomaterial Surface", dated Dec. 1988.

Samuels et al., "An Electrode-Supported Oxidation Catalyst Based on Ruthenium(IV). pH 'Encapsulation' in a Polymer Film," J. Am. Chem Soc., vol. 103, pp. 307–312 (1981).

Denisevich et al., "Unidirectional Current Flow and Charge State Trapping at Redox Polymer Interfaces on Bilayer Electrodes: Principles, Experimental Demonstration, and Theory," J. Am. Chem. Soc., vol. 103, pp. 4727–4737 (1981).

Abruna et al., "Rectifying Interfaces Using Two-Layer Films of Electrochemically Polymerized Vinylpyridine and Vinylbipyridine Complexes of Ruthenium and Iron on Electrodes," J. Am. Chem. Soc., vol. 103, pp. 1–5 (1981).

Ellis et al., "Selectivity and Directed Charge Transfer Through an Electroactive Metallopolymer Film," J. Am. Chem. Soc., vol. 103, pp. 7480–7483 (1981).

Degani, Y. and Heller, A., "Direct Electrical Communication Between Chemically Modified Enzymes and Metal Electrodes. 1. Electron Transfer from Glucose Oxidase to Metal Electrodes via Electron Relays, Bound Covalently to the Enzyme," Journal of Physical Chemistry, vol. 91, pp. 1285–1289 (1987).

Degani, Y. and Heller, A., "Direct Electrical Communication Between Chemically Modified Enzymes and Metal Electrodes. 2. Methods for Bonding Electron-Transfer Relays to Glucose Oxidase and D-Amino-Acid Oxidase," JACS, vol. 110, pp. 2615–2620 (1988).

FIG.2A
POLYMER A
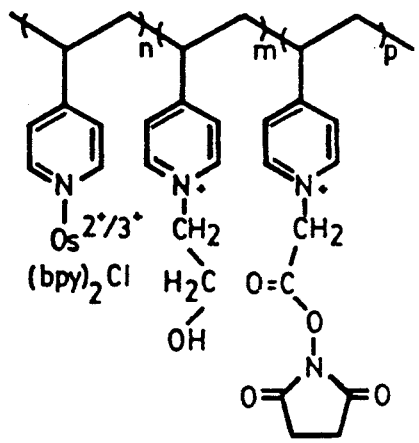
FIG.2B
POLYMER B
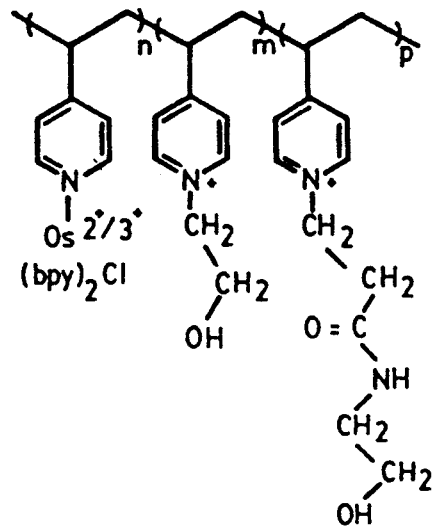
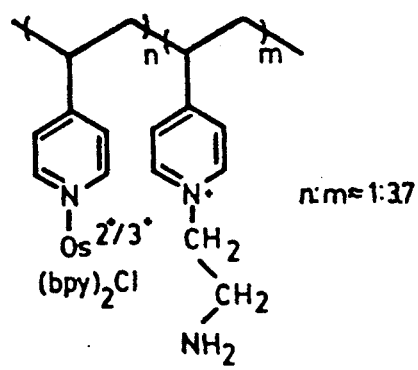
POLYMER C
FIG.2C
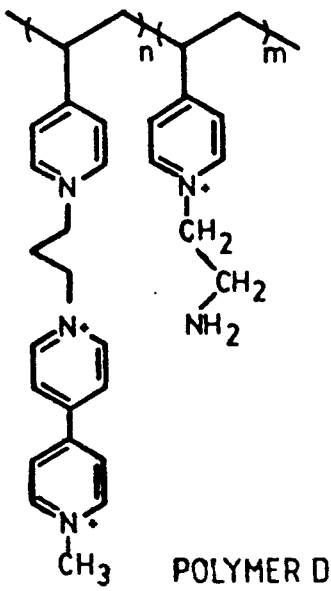
POLYMER D
FIG.2D

POLYMER E

FERROCENE

POLYMER F

POLY

POLYMER G

PEG-DGE  FIG. 3A
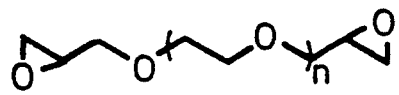
EPOXIDE REACTION WITH AN AMINE  FIG. 3B
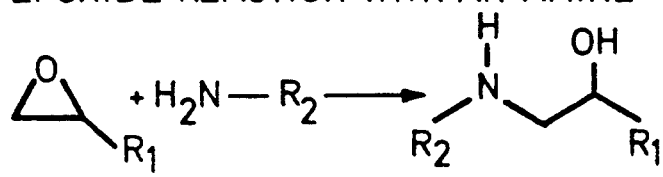
CYANURIC CHLORIDE  FIG. 3C
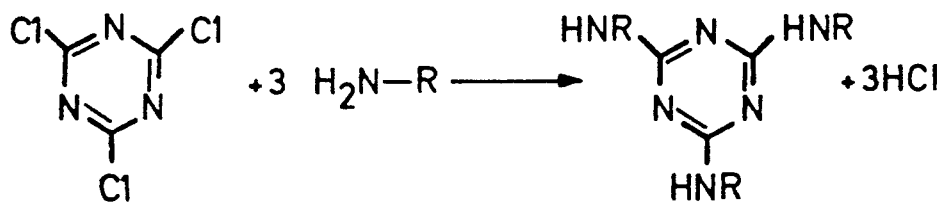
N-HYDROXYSUCCINIMIDE ESTERS  FIG. 3D
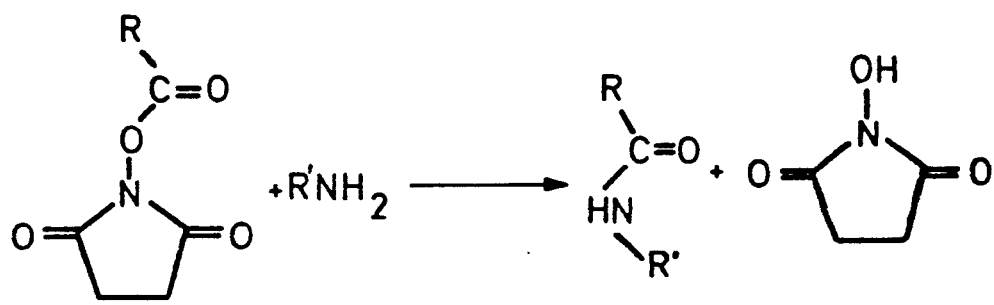

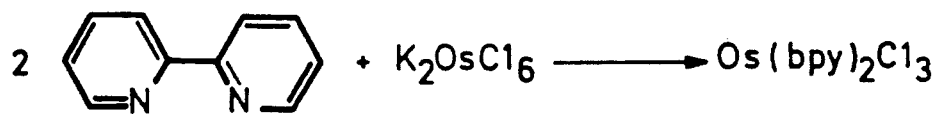
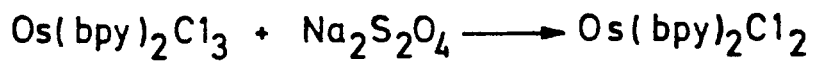
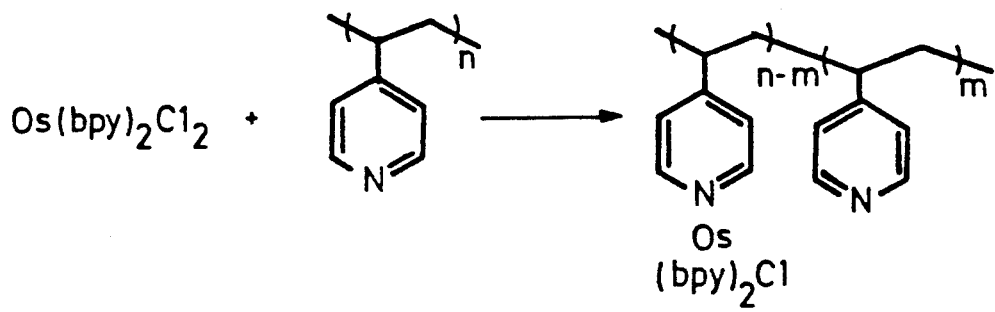
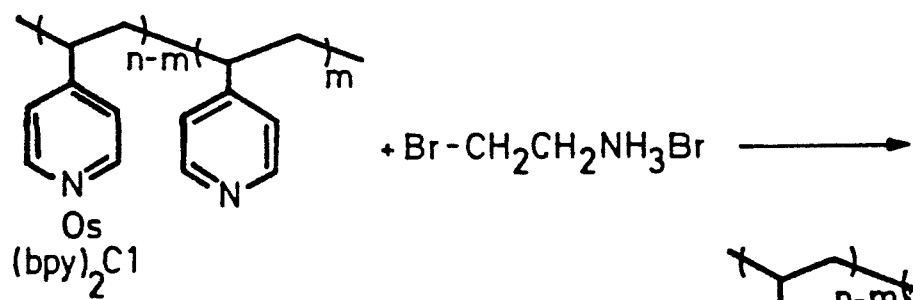
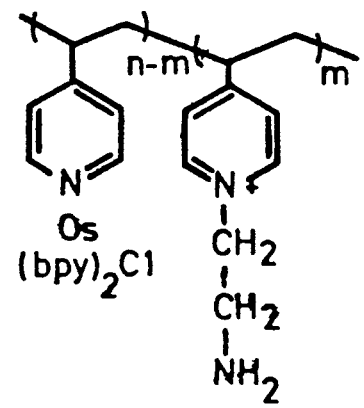
FIG.4
POLYMER C

ENZYME ELECTRODES

The Government may own certain rights in this invention pursuant to Office of Naval Research Contract No. N00014-88-K-0401.

BACKGROUND OF THE INVENTION

1. Field of the Invention

This invention relates to electrodes that can selectively oxidize or reduce a biochemical in a solution. More particularly, it relates to electrodes that can translate the concentration of a biochemical to an electrical current, or can utilize an electrical current to selectively convert one biochemical to another.

2. Description of the Related Art

Enzyme based biosensors (i.e., electrochemical sensors capable of detecting the concentration of a single biochemical species in a medium containing a diverse mixture of other compounds) are used in an increasing number of clinical, environmental, agricultural and biotechnological applications. Amperometric enzyme electrodes typically require some form of electrical communication between the electrode and the active site of the redox enzyme that is reduced or oxidized by the substrate. However, the electrooxidation of a reduced site or the electroreduction of an oxidized site (the rate, of which is proportional to the concentration of the enzyme substrate) is complicated by the fact that the active site is often located deep inside an insulating protein shell. Thus, redox enzymes such as glucose oxidase do not directly exchange electrons with simple metal electrodes.

Historically, electrical communication between the enzyme and electrode has been achieved through the use of diffusing mediators. The first mediator employed for FAD-enzyme electrodes was the natural substrate of the flavin-linked oxidases, $O_2$. example, the reaction of glucose oxidase (GO) is $$GO\text{-}FAD + glucose \rightarrow GO\text{-}FADH_2 + gluconolactone \quad (1)$$

$$GO\text{-}FADH_2 + O_2 \rightarrow FAD + H_2O_2 \quad (2)$$

and the first commercial amperometric glucose sensors measured either the decrease in $O_2$ concentration at an oxygen electrode, or the increase in $H_2O_2$ concentration at a platinum electrode.

There were several problems associated with such devices: (1) the $H_2O_2$ degraded the enzyme. Nature alleviates this problem through the use of a second enzyme, usually catalase, which is present in high concentrations in cells and catalyses the disproportionation of the $H_2O_2$; (2) the electrode current depended on the concentration of both the enzyme substrates, i.e., both glucose and $O_2$; (3) measurement of the $H_2O_2$ concentration required both a highly catalytic electrode (e.g., Pt) and a potential (ca. 0.7 V vs. SCE) substantially positive of the reversible potential for the FAD/-FADH$_2$ couple (E° is approximately equal to $-0.4$ V vs. SCE). This resulted in large spurious currents due to a number of easily oxidized species in the system to be measured. Because of (2) and (3), the amperometric biosensors were not adequately substance-specific.

The most recent devices have employed small diffusing redox shuttles (Ox/Red) such as ferrocenes, quinones, ruthenium ammines, components of organic metals, and octacyanotungstates. In such electrodes, reaction (1) above is followed by $$GO\text{-}FADH_2 + Ox \rightarrow GO\text{-}FAD + 2\,Red + 2H^+ \quad (3)$$

where the reduced form of the shuttle (Red) is subsequently electrooxidized. Catalase can be added to the system to protect the enzyme from $H_2O_2$. The potential at which these electrodes operate is only slightly positive of the formal potential of the shuttle, and a highly active noble metal electrode is no longer required for the reaction. Thus, the spurious currents due to competing species may be reduced. Still, in an oxygen containing medium, there is a competition between the oxidized form of the shuttle (Ox) and oxygen for the reduced form of the enzyme (GO-FADH$_2$), equations (2) and (3). Thus, the electrode current will be independent of the oxygen concentration only insofar as the shuttle can compete effectively with $O_2$.

Enzyme electrodes such as those just described generally require that the enzyme and shuttle be confined to the proximity of the electrode surface. The small shuttles commonly employed can, however, readily diffuse through the membranes that are needed to contain the enzyme, but permit the passage of the enzyme's substrate, e.g., glucose. Recently, a polymeric redox "wire" based on the poly(vinyl-pyridine) (PVP) complex of Os(bpy)$_2$Cl (abbreviated POs$^{30}$; the bpy of the complex is 2,2'-bipyridine) has been introduced which electrically connects the enzyme to the electrode yet, by virtue of its molecular size, remains confined behind the enzyme-containing membrane. This polycationic redox polymer forms electrostatic complexes with the polyanionic glucose oxidase in a manner mimicking the natural attraction of some redox proteins for enzymes, e.g., cytochrome c for cytochrome c oxidase.

Enzyme electrodes now in use are of several different types. One type of electrode amperometrically measures the oxygen content of gas streams entering and leaving a reactor containing the substrate and its enzyme. If oxygen is involved in the substrate's enzymatic oxidation, its level is depleted and the substrate concentration can be deduced from the decrease in the oxygen content of the gas.

With a second type of enzyme electrode, a natural electroreactive product of the enzyme-catalyzed reaction is amperometrically monitored. For example, the enzymatic reaction of substrates like glucose or lactate with oxygen, catalyzed by some oxidases, produces hydrogen peroxide. Hydrogen peroxide can be electrooxidized and thereby the substrate concentration over a certain range can be translated into a current.

In a third type of enzyme electrode, a non-natural redox couple mediates electron transfer from the substrate-reduced enzyme to the electrode. In this scheme, the enzyme is reduced by its natural substrate at a given rate; the reduced enzyme is in turn, rapidly oxidized by a non-natural oxidizing component of a redox couple that diffuses into the enzyme, is reduced, diffuses out and eventually diffuses to an electrode where it is oxidized. Here again, the oxidation current can be related to the concentration of the substrate. A specific example of such a redox mediator is the ferricinium carboxylate/ferrocene carboxylate couple that diffusionally mediates electron transfer from glucose reduced glucose oxidase to a carbon electrode.

Most natural enzymes are not directly oxidized at electrodes, even if the latter are maintained at strongly oxidizing potentials, without being destroyed. Also they are not reduced at strongly reducing potentials without being decomposed. It has, however, been shown that enzymes can be chemically modified by binding to their proteins redox couples, whereupon, if in the reduced state, they transfer electrons to an electrode. Thus, amperometric glucose sensors have been made with glucose oxidase to which ferricinium/ferrocene functions have been chemically bound. It has also been shown that when redox polycations in solution electrostatically complex polyanionic enzymes, electrons will flow in these complexes from the substrate to the enzyme, and from the enzyme through the redox polymer, to an electrode. Glucose electrodes have also been built with these complexes.

The current produced at a given substrate level can depend on the concentration of the active enzyme molecules. It has been shown that natural reaction products, like hydrogen peroxide, deactivate the enzyme. Enzymes are also continuously denatured. It has been shown that the denaturing of enzymes can be retarded by embedding the enzyme in a rigid three-dimensional polymer structure. It has been suggested that such embedding fixes the protein structure of the enzyme, preventing conformational changes that result in its eventual denaturing. For example, chymotrypsin has been stabilized by embedding it in crosslinked poly(methyl methacrylate).

SUMMARY OF THE INVENTION

Broadly, the invention relates to materials (and films formed from such materials) which include at least two components that can combine to form a three dimensional moleoular structure. At least one of the components comprises a redox compound, and at least one other component comprises an oxidoreductase (hereinafter referred to as a redox enzyme). The resulting three dimensional molecular structure has multiple redox centers and has the redox enzyme bound within.

When such materials are coated onto a surface, the three dimensional molecular structure provides electrical contact between that surface and the redox enzyme. In the three dimensional structure sigma bonds dominate the polymer's backbone, wherefore electron delocalization is limited.

The term "three dimensional molecular structure" as used herein means a structure in which covalent chemical bonds extend in three dimensions. The term is not meant to include a three dimensional structure formed by mere physical bonding of molecules, for example through Van der Waals forces.

The term "redox compound" is used herein to mean a compound that can be oxidized and reduced. The redox compound may have one or more functions that are reducible and oxidizable. Stated another way, the term "redox compound" means a compound which contains one or more redox centers, "redox center" meaning a chemical function that accepts and transfers electrons.

In one embodiment, a material is provided comprising a redox enzyme, a crosslinking agent, and a crosslinkable compound capable of reacting with the crosslinking agent and the redox enzyme. Either the crosslinkable compound or the crosslinking agent, or both, have one or more redox centers. In an alternative embodiment, a material is provided comprising a redox enzyme and a redox compound having two or more functional groups capable of reacting with the enzyme (i.e. a redox compound capable of crosslinking with the enzyme).

When the compounds of each embodiment are mixed together under appropriate conditions, a chemical reaction takes place resulting in the formation of a crosslinked (three-dixensional) redox polymer, with the redox enzyme bound within the crosslinked redox polymer network.

It should be noted that in the alternative embodiment discussed above, the redox enzyme itself is used as the crosslinking agent to crosslink the redox compound into a three dimensional molecular structure. Most (if not all) enzymes have multiple (more than two) functions that can react. Examples of such enzyme functions are amine, phenol, tryptophane, thiol, and imidazole functions.

By "bound within" it is meant that the redox enzyme is contained or incorporated within the crosslinked polymer structure in such a manner that the enzyme will not tend to diffuse out of the structure. Thus, for example, the enzyme may be chemically (covalently) bonded, electrostatically bonded, or hydrogen bonded to the polymer, and not simply physically bound or trapped within cavities of the polymer surface.

The term "crosslinkable compound" is used herein to mean a compound containing at least two groups (i.e., a bi-or-multifunctional compound) capable of reacting with itself or another bi-or-multifunctional compound, resulting in a macromolecule. The term "crosslinking agent" is used herein to mean a compound containing at least two functional groups capable of reacting with and crosslinking other compounds, i.e. it is the substance that crosslinks the crosslinkable compound.

One particularly important application of these materials is in the area of amperometric biosensors. However, it should be understood that these materials have other applications where it is desired to electrically connect redox enzymes to electrodes, as in the electrosyrthesis of biochemicals.

In another broad aspect of the invention, an electrode is provided having a surface coated with a film of a material of the class described above. The term "film" is used broadly to include any coating or layer of the material regardless of thickness or method of application.

In another broad aspect, the present invention pro-. vides for the construction of enzyme electrodes employing this class of materials. This process may involve the mixture of the enzyme and the various polymer components in a common solution followed by the application of the solution to an electrode surface. Various application methods may be used, including (1) addition of drops of the solution onto the electrode surface; (2) dipcoating; (3) spincoating, or (4) spraying the solution onto the electrode surface. The application step is followed by a curing step such as drying in air or vacuum.

Alternatively, the process may involve the addition of the enzyme and polymer components in separate solutions to the surface of the electrode, mixing, and then curing in air or vacuum.

The preferred crosslinkable compounds for use in this invention are hydrophilic, containing chemical groups such as alcohols, carboxylic acids, amines, amides, sulfonates, sulfates, phosphates and phosphonates. Such groups tend to promote the solubility of the components in water which facilitates contact with the water soluble enzymes. Such groups may also improve the stability of the immobilized enzyme against denaturation.

The redox compounds (or redox centers contained within compounds) used in this invention may be either organic or inorganic. Transition metal complexes with organic ligands such as bipyridine or cyclopentadiene are often preferred as redox centers because of their chemical stability in various oxidation states and their facile electron transfer kinetics. Typical examples of such complexes are the polypyridine complexes of di-or trivalent osmium ions and the various derivatives of ferrocene (bis-cyclopentadienyl iron) or cobaltocene (bis-cyclopentadienyl cobalt). However, a number of organic redox centers may also be employed. The various derivatives of viologen (N,N'-bis alkyl-4,4'-bipyridine) constitute typical examples of this class.

The preferred crosslinking agents are water soluble compounds that react under conditions where most enzymes are stable, that is around pH 7 and room temperature. Included in this category of crosslinking agents are multifunctional epoxides, aldehydes, imidoesters, N-hydroxysuccinimide esters and carbodiimides. A number of reagents with limited solubility in water may also be used by dissolving them in a water-miscible organic solvent such as acetone, methanol, acetonitrile or dimethylformamide. Included in this category are reagents such as cyanuric chloride, tetrachlorobenzoquinone, benzoquinone and tetracyanoquinodimethane. These reagents may react with one or more types of functions including amines, alcohols, thiols and carboxylic acids which may be present on the surface of enzymes and may also be included in the structure of the redox compound.

The electrodes to which the crosslinked redox polymer is applied can be made of any of a number of metals, semi-metals, or semiconductors. For example, gold, platinum, glassy carbon, or graphite electrodes may be used.

In one preferred embodiment, osmium bis(2,2'bipyridine) dichloride is coordinated to a poly(vinyl-pyridine) chain forming approximately one osmium bis(bipyridine) vinylpyridine chloride complex per five vinylpyridine units. The remaining vinylpyridines are quaternized with bromoethylamine hydrobromide, leading to a very hydrophilic redox polymer containing pendant ethylamine groups. This polymer may be dissolved in an aqueous solution containing the enzyme and a water soluble diepoxide, such as poly(ethylene glycol diglycidyl ether). Upon applying the solution onto an electrode surface and drying in air or vacuum, the epoxide may react with both the ethylamine pendant groups of the redox polymer and the surface lysine residues of the enzyme. This results in an enzyme-containing crosslinked redox polymer film on the electrode surface.

The method of operation of such an enzyme electrode may be illustrated using a glucose electrode as an example. Upon immersion of the electrode into a solution containing glucose, the glucose diffuses into the film where it may react with the glucose oxidase enzyme forming gluconolactone and the reduced form of the enzyme. The reduced enzyme may then be oxidized by the osmium complex-containing polymer. Electrons are subsequently transferred through the polymer to the electrode. Thus, an electrical current proportional to the concentration of the enzyme substrate is achieved.

Electrons from a substrate-reduced enzyme can be transferred either to the enzyme's natural re-oxidizer (oxygen in the case of glucose oxidase, lactate oxidase and other flavoenzymes) or, via the redox-centers of the polymer to the electrode. Only the latter process contributes to the current. Thus, it is desirable to make the latter process fast relative to the first. This can be accomplished by (a) increasing the concentration of the redox centers (e.g. the number of osmium complexes) in the film, or (b) assuring that these centers are fast, i.e. that they are rapidly oxidized and reduced. It is also desirable to make the redox centers oxidizing with respect to the reduced enzyme. This often increases the rate of transfer of electrons to the electrode.

However, it is also true that the higher the oxidation potential of the redox couple, the more extraneous compounds may be oxidized by it, that is, the less selective is the electrode. Thus, there is an optimum range of oxidation potential for the redox couple for any given application. Similar arguments hold for electrodes which will be used in the reduction of enzymes.

It should be appreciated that this description applies equally to the operation of a biosensor (in the above case, a glucose sensor) or an electrosynthesizer of biochemicals (in this case, gluconolactone, the product that is electrosynthesized). Thus, although in practice, the two devices may be differently configured, the scope of the present invention encompasses both biosensors and bioelectrosynthesizers, and related devices.

BRIEF DESCRIPTION OF THE DRAWINGS

FIG. 2 shows several examples of redox centers bound to multifunctional compounds capable of forming crosslinked polymers when reacted with crosslinking agents, including enzymes or other multifunctional compounds, in accordance with the present invention.

FIG. 2A shows a crosslinkable redox compound, Polymer A.

FIG. 2B shows a corsslinkable redox compound, Polymer B.

FIG. 2C shows a crosslinkable redox compound, Polymer C.

FIG. 2D shows a crosslinkable redox compound, Polymer D.

FIG. 3 shows several examples of crosslinking agents used by the present invention and some of the typical reactions which they undergo.

FIG. 3A shows the epoxide crosslinking agent PEG-DGE.

FIG. 3B shows reaction of PEG-DGE with amine.

FIG. 3C shows reaction of the crosslinking agent cyanuric chloride with amine.

FIG. 3D shows reaction of the crosslinking agent N-Hydroxysuccinimide with an amine.

FIG. 4 shows a synthetic scheme for one of the preferred crosslinkable redox polymers as provided by the present invention.

DETAILED DESCRIPTION OF THE PREFERRED EMBODIMENTS

Figure 1:
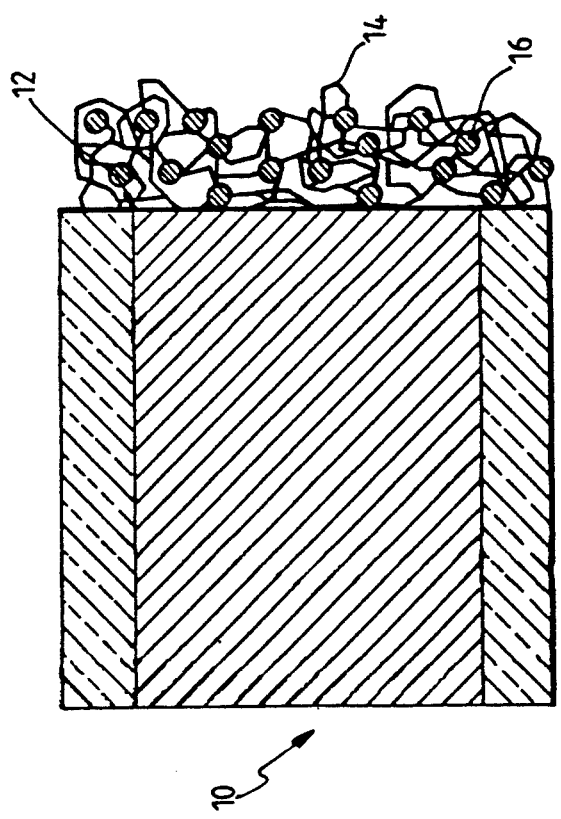
FIG. 1 is a schematic drawing of a crosslinked redox polymer-enzyme electrode as provided by the present invention.

The materials and processes provided by the present invention, the crosslinked redox polymers and the incorporation of redox enzymes in them, have particularly important applications in the manufacture of enzyme electrodes of the type illustrated in FIG. 1. These electrodes may be used in such applications as amperometric biosensors and the electrosynthesis of biochemicals.

There are several advantages to an enzyme electrode system based on a crosslinked redox polymer. First, the use of crosslinked films on the electrode surface eliminates the requirement for a membrane which is often required in conventional systems to confine the enzyme to a small volume close to the electrode surface. Thus, the use of crosslinked redox films tends to simplify the design and the manufacture of the enzyme electrode. Second, the process by which the electrodes are produced is relatively simple, reproducible and can be easily automated. Third, the enzyme may be stabilized by its interaction with the polymer matrix, thus retarding thermal denaturation. Also, it may be physically protected from attack by proteases in solution which are too large to diffuse through the polymer film. Fourth, the versatility of these materials allows the tailoring of properties for specific applications. For example, the redox potential, the hydrophilicity and the charge on the polymer may be adjusted as may the crosslinking method. Fifth, the transport of interfering electroreactive substances to the electrode surfaces and/or their adsorption on these surfaces can be retarded by appropriate design of the polymer. Sixth, the resulting electrodes are in general mechanically rugged and typically exhibit excellent stability during storage. Seventh, although enzymes are known to rapidly denature on many surfaces, the polymer apparently tends to protect the enzymes from the surface of the electrode. Thus, virtually any electrode surface may be used for these enzyme electrodes. Additionally, such polymers in general appear to be substantially biocompatible.

In one preferred embodiment, the water soluble crosslinking agent polyethylene glycol diglycidylether (PEG-DGE, FIG. 3) is used to react with redox compounds with amine functions and with amine functions of the lysine groups of the enzyme. The reaction between epoxides and amines is particularly advantageous since the reaction (1) releases no low molecular weight species; (2) does not greatly change the local pH; (3) does not greatly change the charge on either the redox compound or the enzyme; and (4) is compatible with a number of different enzymes. PEG-DGE is also commercially available in a number of chain lengths. The reaction between PEG-DGE and amines proceeds very slowly in dilute aqueous solution. Thus, all the reactants may be combined in a single solution before the application step which greatly simplifies the manufacture of the electrodes. The crosslinking reaction may then proceed to completion when the solution is dried on the surface of the electrode. The cure time for the film is 24 to 48 hours at room temperature.

An enzyme electrode as provided by the present invention is shown schematically in FIG. 1. The electrode 10 has a surface 12 which is coated with a crosslinked redox polymer film 14. A redox enzyme 16 is bound to the polymer 14. The polymer 14 electrically connects the electrode 10 to the enzyme 16.

Figure 2E:
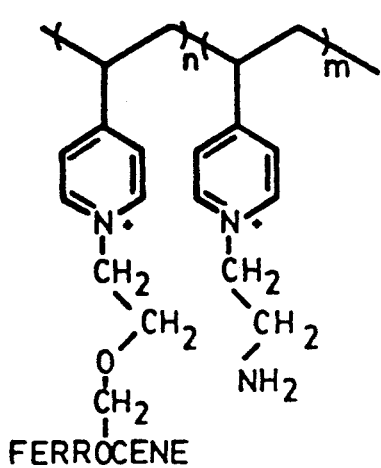
FIG. 2E shows a crosslinkable redox compound, Polymer E.
Figure 2F:
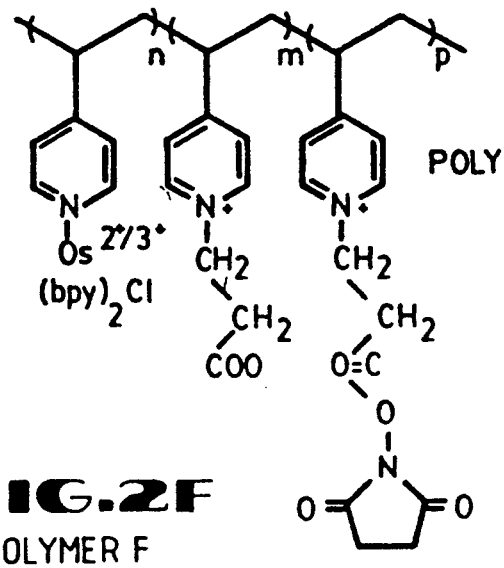
FIG. 2F shows a crosslinkable redox compound, Polymer F.
Figure 2G:
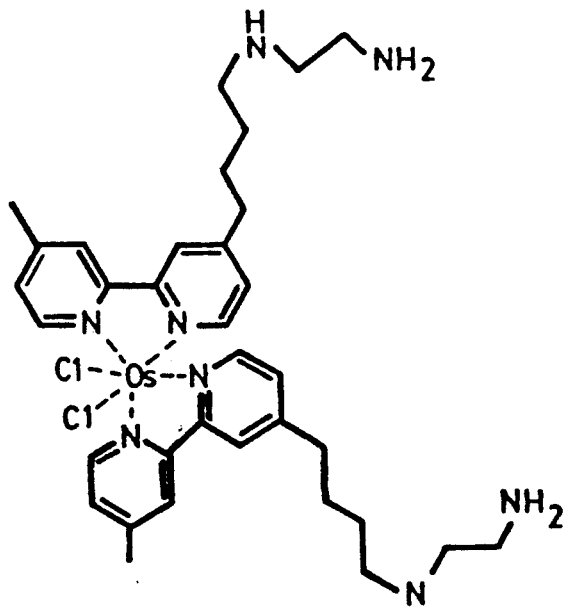
FIG. 2G shows a crosslinkable redox compound, Polymer G.

Various preferred crosslinkable compounds containing redox active centers are shown in FIG. 2. Polymer A and Polymer F are representative of that class of compounds which require only the addition of enzymes to form crosslinked films, i.e. the enzyme is the only required crosslinking agent. The other compounds are representative of that class of compounds which do not react directly with chemical functions on the enzyme. They therefore require a separate crosslinking agent such as those illustrated in FIG. 3.

FIG. 3 shows three representative classes of crosslinking agents, and their reactions with a typical organic compound having an amine group, represented as $RNH_2$. The crosslinking agents shown are an epoxide (e.g. PEG-DGE), cyanuric chloride, and an N-Hydroxysuccinimide.

Figure 5:
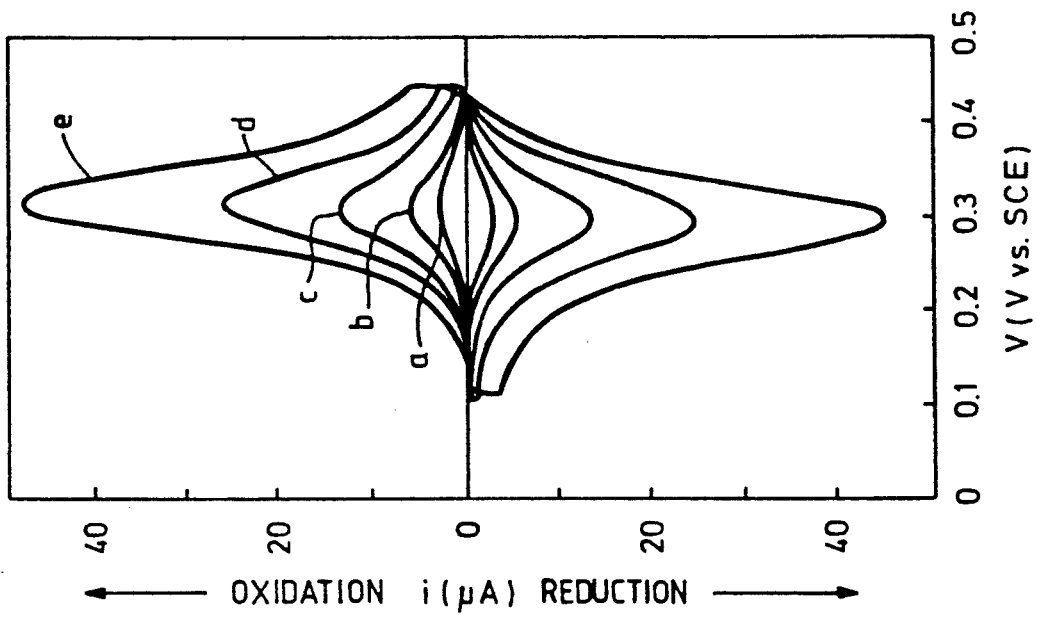
FIG. 5 shows a number of cyclic voltammograms of a crosslinked redox polymer film containing glucose oxidase prepared according to the present invention. There is no glucose in solution. Scan rates (mV/s)(a) 10, (b) 20, (c) 50, (d) 100, (e) 200.

Characteristic cyclic voltammograms of a film containing Polymer F, glucose oxidase and triethylenetetraamine in the absence of glucose on glassy carbon are shown in FIG. 5. The almost symmetrical shape of the oxidation and reduction waves, and the fact that the peak currents do not decrease over time show that the polymer film is strongly attached to the electrode surface and in good electrical contact with it. The fact that the peak shape changes very little upon increasing the scan rate from 10 mV/s to 200 mV/s is evidence for fast electron transfer through the polymer film.

Figure 6:
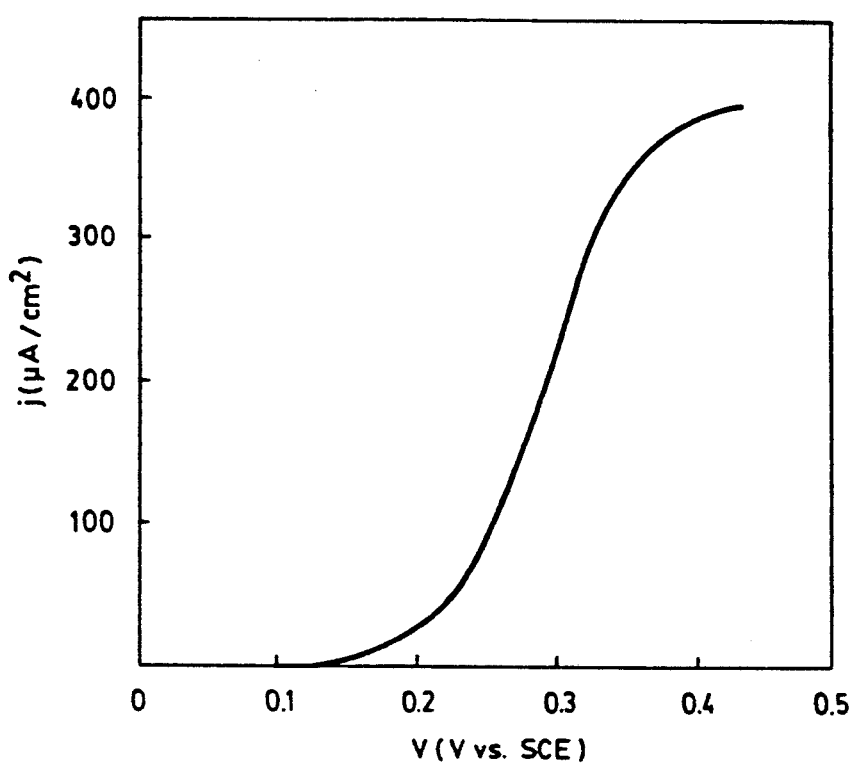
FIG. 6 shows a cyclic voltammogram of the film used in FIG. 5 after addition of 40 mM glucose. Scan rate 5 mV/s.

FIG. 6 shows a cyclic voltammogram of the same film as FIG. 5 after the addition of glucose to a final concentration of 40 mM. A catalytic oxidation is exhibited as the electrons are transferred from the glucose-reduced enzyme to the redox polymer and from the redox polymer to the electrode.

Figure 7:
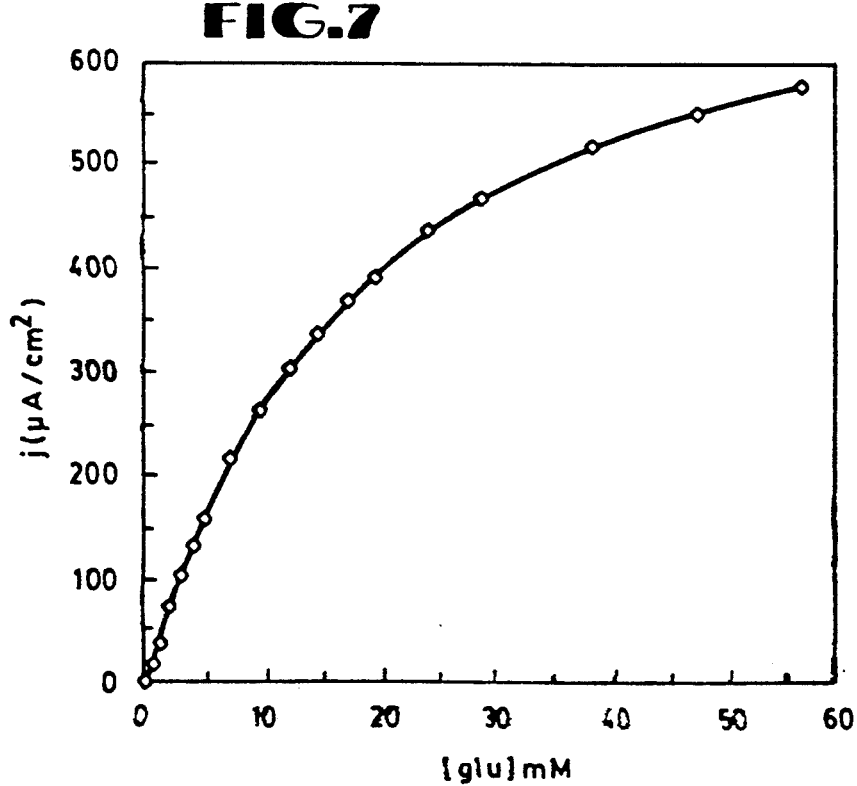
FIG. 7 shows a typical response curve (current density versus substrate concentration) for a glucose electrode prepared in accordance with the present invention.

A typical response curve of a Polymer C-glucose oxidase-PEG-DGE film is shown in FIG. 7. As the glucose concentration is increased the current response follows the characteristic Michaelis-Menten behavior of the enzyme.

EXAMPLES

The following examples are designed to illustrate certain aspects of the present invention. The examples are not intended to be comprehensive of all features and all embodiments of the present invention, and should not be construed as limiting the claims presented herein.

EXAMPLE 1

The synthetic scheme for this example is illustrated FIG. 4. cis - Bis(2,2'-bipyridine-N,N') dichloroosmium (II) ($Osbpy_2Cl_2$) was prepared by a standard literature procedure (Lay, P.A.; Sargeson, A.M.; Taube, H., Inorg. Syn. 1986, 24, 291). Polyvinylpyridine (PVP), nominal molecular weight 50,000, was purchased from Polysciences, Inc. and purified three times by dissolution in methanol and precipitation with ether. 0.494 gram $Os(bpy)_2Cl_2$ and 0.430 gram PVP were added to 18 mls. of ethylene glycol in a round bottom flask under nitrogen. The mixture was slowly heated to reflux (196° C.) and maintained at reflux for about 105 minutes. It was then cooled to room temperature and 30 mls. of dimethylformamide (DMF) was added. 1.5 gram bromoethylamine hydrobromide was added to the mixture which was then stirred at about 35° C. overnight. The polymer solution was then poured into a rapidly stirred solution of acetone and the precipitate was filtered, washed with acetone and stored in a vacuum dessicator. The approximate structure of this polymer is shown in FIG. 2 (Polymer C).

Three solutions were made up in aqueous 10 mM HEPES buffer at pH 8:1:
  Solution 1 contained 10 mg/ml polymer C
  Solution 2 contained 5 mg/ml glucose oxidase
  Solution 3 contained 2.7 mg/ml PEG-DGE The enzyme containing solution was made up fresh every day; the other two solutions were stable for at least one month. 15 microliters of solution 1, 15 microliters of solution 2 and 5 microliters of solution 3 were thoroughly mixed in a vial and 3 microliters of the mixture was deposited onto a glassy carbon disk electrode (4.5 mm in diameter). The electrode was then placed in a vacuum dessicator for 24 hours. Upon exposure to solutions containing high concentrations of glucose ($\geq 60$ mM), such electrodes commonly exhibited current densities of 400-1100 microA/cm$^2$ at a potential in the 0.35-0.45 volt range measured relative to the potential of the Standard Calomel Electrode (SCE). In the absence of glucose, the current density was approximately 1 microA/cm$^2$.

EXAMPLE 2

The procedure of Example 1 was repeated but cyanuric chloride was used as the crosslinking agent in place of PEG-DGE. In this case the polymer and enzyme were made up in 100 mM phosphate buffer solution at pH 7.1. 2 microliters each of the polymer and enzyme solution were mixed on the electrode surface with 0.5 microliters of an acetonitrile solution of cyanuric chloride (20 mM). This crosslinking reaction is quite fast and the electrode films required a curing time of only about 30 minutes in air or vacuum. Upon exposure to solutions containing high concentrations of glucose ($\geq 60$ mM), such electrodes commonly exhibited current densities of 80-120 microA/cm$^2$ at a potential in the 0.35-0.45 volt range measured relative to the SCE. In the absence of glucose, the current density was approximately 1 microA/cm$^2$.

EXAMPLE 3

9.6 mls. bromoacetyl chloride was dissolved in 120 ml of methylene chloride and cooled to 0° C. under nitrogen. 13.4 gram N-hydroxysuccinimide and 11.8 gram triethylamine were dissolved in 50 ml of methylene chloride and slowly dripped into the cold solution of acid chloride over 30 minutes. The solution was stirred for an additional 20 minutes. Then ice water was added, the phases were separated, the organic phase was washed two more times with ice water, once with saturated sodium chloride solution and dried over magnesium sulfate. The solution was concentrated under vacuum until crystals started to appear. Then hexane was added and the solution was cooled to 0° C. The crystals of bromoacetoxysuccinimide were filtered and dried in a vacuum dessicator.

0.507 gram Osbpy$_2$Cl$_2$ and 0.507 gram PVP were reacted in refluxing ethylene glycol for 30 minutes, the solution was then cooled, 20 mls. of acetone was added and the mixture was poured into rapidly stirred ethyl acetate. The resulting polymer (PVP-Osbpy$_2$Cl) was filtered and dried in vacuum.

0.31 gram PVP-Osbpy$_2$Cl and 0.12 gram 2-bromoethanol were dissolved in 25 mls. DMF and refluxed for 30 minutes. Then about 1 gram (a large excess) of bromoacetoxysuccinimide was added and the solution was heated at 40° C. for about 2 hours. It was then cooled, poured into stirred acetone, filtered and stored in a vacuum dessicator. This procedure led to a polymer whose approximate structure is shown in FIG. 2 (Polymer A).

A solution of 22 mg/ml Polymer A in deionized water was prepared immediately before use. Another solution in 0.1 M HEPES buffer was prepared containing 22 mg/ml glucose oxidase and 1.1 microliter/ml catalase solution. 10 microliters of each solution were mixed on the surface of a 6 mm diameter graphite rod electrode and cured at room temperature for 24 hours in vacuum. In a solution containing 31 mM glucose, this electrode exhibited a current density of about 300 microA/cm$^2$ when held at a potential of 0.45 volt relative to the SCE. Under these conditions, but in the absence of glucose, the electrode gave a background current density of about 4 microA/cm$^2$. In such films the polymer probably reacts with the lysines on the enzyme surface resulting in a crosslinked film. Small amounts of an additional polyamine, for example, triethylenetetraamine, may also be added to such films to improve their physical properties.

EXAMPLE 4

The synthetic procedure of Example 3 was repeated with the substitution of 3-bromopropionyl chloride for bromoacetyl chloride. The resulting polymer containing esters of hydroxysuccinimide was dispersed in DMF and a large excess of ethanolamine was added. The mixture was stirred overnight at room temperature, filtered and poured into stirred tetrahydrofuran (THF). The precipitate was filtered and dried. This procedure led to a polymer whose approximate structure is shown in FIG. 2 (Polymer B).

Three solutions were made up in 10 mM HEPES at pH 8.4:
  Solution 1 contained 10 mg/ml Polymer B
  Solution 2 contained 8 mg/ml glycerol-3-phosphate oxidase
  Solution 3 contained 4 mg/ml cyanuric chloride in acetonitrile 5 microliters each of solutions 1 and 2 were mixed on the surface of a glassy carbon disk electrode with 2 microliters of solution 3. The electrode was dried in vacuum for 50 minutes. In the presence of 10 mM L-alpha-glycerophosphate this electrode exhibited a current density of 30 microA/cm$^2$ when held at a potential of 0.45 volts relative to the SCE reference. In the absence of a L-alpha-glycerophosphate, the current density was 1.1 microA/cm$^2$ at the same potential.

EXAMPLE 5

N-methyl-4,4'-bipyridinium iodide (monoquat) was synthesized by a standard technique. 1.13 gram monoquat was dissolved in 70 mls. acetonitrile and 25 mls. DMF. 9.0 mls. 1,4-dibromobutane was added and the solution was refluxed overnight. It was then cooled, the precipitate was filtered, washed with acetone and dried. The mixed bromo,iodo salt of the resulting viologen was dissolved in water, filtered and precipitated as the hexafluorophosphate (PF$_6$) salt through addition of ammonium hexafluorophosphate. This was filtered and dried in vacuum.

0.50 gram PVP and 1.50 gram viologen were dissolved in 60 mls. of DMF and heated to 68° C. overnight. Then about 2grams of 2-bromoethylamine hydrobromide was added to the war solution. After about 90 minutes, the DMF was decanted from the precipitated polymer, and the polymer was dissolved in water, filtered and precipitated as the $PF_6$ salt. This was dried, then redissolved in DMF containing 2-bromoethylamine hydrobromide. After further warming at 68° C. overnight, much of the polymer had precipitated. Tetrabutyl ammonium bromide was added to precipitate the rest which was filtered and washed with methylene chloride. The very hygroscopic polymer was stored in a vacuum dessicator. The approximate structure of this polymer (Polymer D) is shown in FIG. 2.

Three solutions were made up in 10 mM HEPES buffer at pH 8:1:

Solution 1 was 5 mg/ml Polymer D
Solution 2 was about 5 mg/ml nitrate reduces
Solution 3 was 2.7 mg/ml PEG-DGE 25 microliters of solutions 1 and 2 were thoroughly mixed with 10 microliters of solution 3. 4 microliters of this mixture was applied to the surface of a 3 mm diameter glassy carbon disk electrode and cured overnight in a vacuum at room temperature. Upon exposure of this electrode to a deaerated solution containing 25 mM nitrate, a reduction current density of 22.6 microA/cm$^2$ was recorded at a potential of $-0.8$ volts relative to the SCE reference. Under the same conditions in the absence of nitrate ion the background current density was 7.0 microA/cm$^2$.

EXAMPLE 6

4'-Methyl,4'-(4-bromobutyl) bipyridine, made from the monolithium salt of dimethylbipyridine and 1,4-dibromobutane, was used as a starting material. 1.11 gram of this was dissolved in 50 mls. of ethylene diamine and warmed to about 80° C. for 2.5 hours. The solvent was then removed under vacuum, the residue was dissolved in ethyl acetate and the product was extracted into aqueous solution at pH 5.1. The aqueous solution was washed with methylene chloride. It was then made basic and the product was extracted into methylene chloride, washed with water, dried and evaporated.

190 mgs of the resulting 4-methy1,4'-(butylaminoethylamine) bipyridine was dissolved in 4 mls. DMF and 144 mgs of $K_2OsCl_6$ was added and refluxed for 1 hour. Water and dilute HCl were added to the DMF solution, it was filtered and the product was precipitated by the addition of ammonium hexafluorophosphate. The product was dried under vacuum. The structure of this compound is shown in FIG. 2 (Polymer G).

A 3mm glassy carbon disk electrode was made by applying 3 microliters of 5 mg/ml glucose oxidase in 10 mM HEPES buffer pH 8.1, 1 microliter of 2.7 mg/ml PEG-DGE in the same buffer and 3 microliters of 10 mg/ml Polymer G in acetonitrile. The electrode was cured overnight in vacuum. Upon exposure to a solution containing a high concentration of glucose ($\geq 60$ mM), this electrode exhibited a current density of 2.1 microA/cm$^2$ when held at a potential of 0.15 V relative to the SCE reference. The background current density in the absence of glucose was 0.84 microA/cm$^2$ at the same potential.

This invention has been disclosed in connection with specific embodiments. However, it will be apparent to those skilled in the art that variations may be undertaken without departing the spirit and scope of the invention.

What is claimed is:

1. An electrode having a surface coated with a film, the film comprising:
   a crosslinked polymer having multiple redox centers; and
   a redox enzyme bound within the crosslinked polymer,
   wherein the crosslinked polymer provides electrical contact between the electrode and the enzyme.

2. The electrode of claim 1, wherein the crosslinked polymer includes a plurality of transition metal complexes, each complex having a plurality of organic ligands.

3. The electrode of claim 2, wherein the transition metal comprises osmium.

4. The electrode of claim 1, wherein the crosslinked polymer includes a plurality of organic redox centers.

5. An amperometric biosensor having an electrode as recited in claim 1.

6. The amperometric biosensor of claim 5, wherein the electrode is capable of selectively sensing one of the following biochemicals: glucose, lactate, glycerol-3-phosphate, L-amino acids, or D-amino acids.

7. The amperometric biosensor of claim 5, wherein the electrode is capable of selectively sensing nitrate.

8. A bioelectrosynthesizer having an electrode as recited in claim 1.

9. The electrode of claim 1, wherein the redox enzyme is covalently bonded to the crosslinked polymer.

10. An electrode having a surface coated with a film, the film comprising:
    a hydrophilic cross-linked polymer having multiple redox centers; and
    a redox enzyme bound within the cross-linked polymer, wherein the cross-linked polymer provides electrical contact between the electrode and the enzyme.

11. An electrode made of a material selected from the group consisting of gold, platinum, glassy carbon and graphite, said electrode having a surface coated with a film, the film comprising:
    a cross-linked polymer having multiple redox centers; and
    a redox enzyme bound within the cross-linked polymer, wherein the cross-linked polymer provides electrical contact between the electrode and the enzyme.

12. The electrode of claim 11, wherein the resulting electrode exhibits current densities in excess of 10 micro Amps/cm$^2$ in the presence of substrate.

13. The electrode of claim 12, wherein the resulting electrode exhibits current densities in excess of 100 micro Amps/cm$^2$ in the presence of substrate.

14. The electrode of claim 13, wherein the resulting electrode exhibits current densities in excess of 1000 micro Amps/cm$^2$ in the presence of substrate.

15. An electrode having a surface coated with a film, the film comprising:
    a cross-linked polymer having multiple redox centers; and
    a redox enzyme bound within the cross-linked polymer, wherein the cross-linked polymer provides electrical contact between the electrode and the enzyme, and wherein the resulting electrode has an operating potential in the range of 0.1V to 0.5V versus the Standard Calomel Electrode.

16. An electrode having a surface coated with a film, the film comprising:

a cross-linked polymer having multiple redox centers; and a redox enzyme bound within the cross-linked polymer, wherein the cross-linked polymer provides electrical contact between the electrode and the enzyme, and wherein the resulting electrode exhibits current densities in excess of 10 micro Amps/cm$^2$ in the presence of substrate.

17. The electrode of claim 16 wherein the resulting electrode exhibits current densities in excess of 100 micro Amps/cm$^2$.

18. The electrode of claim 17 wherein the resulting electrode exhibits current densities in excess of 1000 micro Amps/cm$^2$.

* * * * *